United States Patent [19]

Ruggera

[11] Patent Number: 5,052,997
[45] Date of Patent: Oct. 1, 1991

[54] DIATHERMY COIL

[75] Inventor: Paul S. Ruggera, McLean, Va.

[73] Assignee: The United States of America as represented by the Secretary of the Department of Health and Human Services, Washington, D.C.

[21] Appl. No.: 37,203

[22] Filed: Apr. 10, 1987

[51] Int. Cl.⁵ ............................................. A61N 1/40
[52] U.S. Cl. .................................. 600/13; 128/419 F; 219/10.79
[58] Field of Search .................... 128/804, 419 F, 399, 128/402; 600/13, 14; 336/224, 225; 219/10.79

[56] References Cited

U.S. PATENT DOCUMENTS

| | | |
|---|---|---|
| 1,394,810 | 10/1921 | Craddick .............................. 600/13 |
| 3,622,280 | 11/1971 | Keller . |
| 3,890,953 | 6/1975 | Kraus et al. . |
| 3,915,151 | 10/1975 | Kraus . |
| 4,030,480 | 6/1977 | Meyer . |
| 4,056,097 | 11/1977 | Maass . |
| 4,066,065 | 1/1978 | Kraus . |
| 4,186,729 | 2/1980 | Harrison . |
| 4,266,532 | 5/1981 | Ryaby et al. . |
| 4,392,040 | 7/1983 | Rand et al. . |
| 4,412,540 | 11/1983 | Bentall . |
| 4,501,265 | 2/1985 | Pescatore . |
| 4,527,550 | 7/1985 | Ruggera et al. . |
| 4,550,714 | 11/1985 | Talish et al. . |
| 4,587,978 | 5/1986 | Suyama et al. . |
| 4,589,423 | 5/1986 | Turner . |
| 4,616,629 | 10/1986 | Moore . |

FOREIGN PATENT DOCUMENTS

| | | |
|---|---|---|
| 1113156 | 11/1981 | Canada . |
| 0144920 | 6/1985 | European Pat. Off. . |
| 2523450 | 9/1983 | France .................................. 600/13 |
| 1132960 | 1/1985 | U.S.S.R. ............................ 128/804 |

OTHER PUBLICATIONS

"Development of Family of RF Helical Coil Applicators which Product Transversely Uniform Axially Distributed Heating in Cylindrical Fat-Muscle Phantoms", Ruggera and Gideon Kantor, IEEE Transactions on Biomedical Engineering, vol. BME-31, No. 1, Jan. 1984.

Primary Examiner—Lee S. Cohen
Attorney, Agent, or Firm—John E. Tarcza

[57] ABSTRACT

A short but large apertured coil of the sloped-helix type allows deep heating of a part of the human body by RF waves, for example with a three-turn coil having a central part wherein parts of a pair of turns are parallel. The length of the coil equals two wavelengths of the RF wave. Each loop or turn is widened with for instance a conducting ribbon, having specific twists to provide corresponding vertical and horizontal parts if the coil is considered to have its axis aligned vertically.

20 Claims, 3 Drawing Sheets

DIATHERMY COIL

BACKGROUND OF THE INVENTION

The invention is directed to an oval-apertured, unevenly-spaced, three-turn coil with reflectors and shields, for depositing uniform heat in biological tissues at radiofrequencies.

Diathermy machines are known in the prior art, for instance as described by a patent and article of Ruggera et al[1]. The prior art coil described in the patent requires a four-to-one ratio of the length to the diameter for efficient (full-wave) uniform cross-sectional heating. A coil following this design and having a diameter of 60 cm would require a length of 240 cm (approximately 8 feet long). This was considered by clinicians to be a severe limitation, in that the whole body would have to be placed in the coil for treatment, thereby potentially heating unintended areas. Further, the longitudinal heating about the center of the coil's length occurs for approximately 30 cm out to the half-power points, and 60 cm is too large for most tumor treatments. Additionally the physical appearance and size of such a coil would present aesthetic and practical problems in a typical clinical setting. [1] U.S. Pat. No. 4,527,550, "Helical Coil for Diathermy. Apparatus", issued 9 July 1985; and "Development of Family of RF Helical Coil Applicators which Produce Transversely Uniform Axially Distributed Heating in Cylindrical Fat-Muscle Phantoms", *IEEE Transactions on Biomedical Engineering*, Vol. BME-31, No. 1, Jan. 1984.

SUMMARY OF THE INVENTION

The present invention is directed to a coil for producing uniform deep heating in biological tissues, using radiofrequency (RF) energy at frequencies from 70 MHz to 110 MHz, without excessive heating of the surface of a body being treated, or of the fat within the body. The coil is of the sloped-helix, double-wave type.

The coil of the present invention has an odd number of turns, preferably three, and the spacing between adjacent loops decreases from both ends of the coil and is constant and small in a center portion of the coil. Loop wideners are provided, at respective angles in different parts of the coil. Reflectors are provided along the coil at respective parts from both ends, near launch points of the RF wave for producing the deep uniform heating.

The present invention provides a device having a large aperture and a short length. It employs air coupling of RF energy, in the near field, to provide advantageously uniform heating. The device is easy to use, light in weight, and uses standard RF power supplies and connections. It is useful for treatment of cancer and for rewarming hypothermia victims.

DESCRIPTION OF PREFERRED EMBODIMENTS

The above prior art article and patent describe applicators and methods for deep heating using a modified device employing a "coil wire-length" resonance. The improved applicator of the present invention also uses the same operational mode, but the length of the coil including the feed lines, if unwound, is approximately equal to two wavelengths of the RF waves used therewith for the heating. Such operation at two wavelengths is discussed in the prior art article above, but only in the context of heating two separate areas simultaneously and with not much uniformity. By incorporating significant physical design changes, it was subsequently found to be possible according to the present invention to deposit deep, longitudinally focused, uniform heating in large elliptical phantoms simulating the human trunk, while using a much shorter coil length, thus overcoming a major disadvantage of the prior art design in the patent above. This was achieved while maintaining a large aperture as required for treatment of the human thorax and abdomen. The resulting length-diameter ratio according to the present invention can be compressed to less than one-to-one. Under the previous design, as the article discusses, excessive surface heating is produced with little central heating. Additionally, the new construction according to the present invention uses an external shield, which minimizes exposure to operating personnel standing alongside the coil during treatment.

The device of the present invention, referred to as of the "sloped helix" type, is an empirically developed design achieved through extensive temperature measurements inside a fat-muscle phantom having a size of the human trunk. The final design presented here produced maximum central heating without excessive surface heating of the phantom. Each of the features of the construction contributed to the final product, namely a short but large-apertured applicator. The sequential construction phases for the sloped helix coil are shown in FIGS. 1-6.

Figure 1:
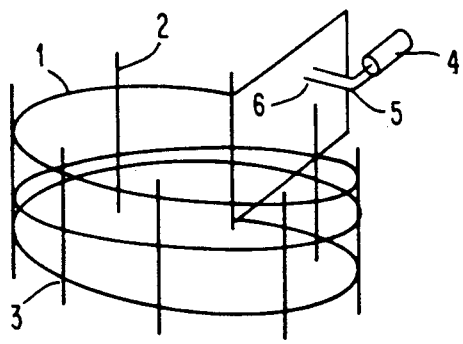
FIG. 1 shows a sloped-helix coil arrangement used in the diathermy device of the present-invention.

In FIG. 1, three turns of ¼ inch diameter tubing 1, preferably of copper, are wound around eight ½ inch diameter plastic, preferably of low dielectric constant to avoid heating during long treatments, e.g. Teflon, supporting rods 2 and secured together at their juncture 3 with plastic, e.g. Teflon, wire ties. These rods can be seen as distributed at the clock positions 12:00, 1:30, 3:00, 4:30, 6:00, 7:30, 9:00 and 10:30, respectively. Tubing is used instead of wire so that water can be circulated thru the windings to keep them cool during prolonged treatments at high RF power. Note that while this design uses unevenly spaced turns, they are symmetrical about the longitudinal center. A coaxial chassis type connector 4 is soldered to the two ends of the tubing surface 5 at the point where it bends to accept the water input. The two ends of the loops and the ends of the tubing are desirably located at the angular position 12:00. This completes the electrical path thru the coil. The tubing ends 6 are smoothed to accept non-conducting, slightly larger diameter tubing through which water for cooling the coil is circulated.

Figure 2:
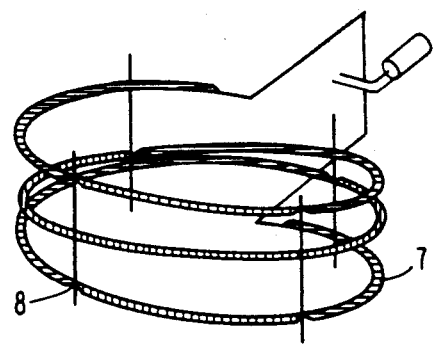
FIG. 2 shows the expanded width of the turns of the coil of FIG. 1, with convolutions of the expanded width, according to the present invention.

In an example as illustrated in FIG. 1, the resulting aperture shape was oval as is the cross-section of the human trunk, with internal major- and minor-axes of 60 cm and 43 cm, respectively, providing a minor to major axis ratio of approximately 0.7. The length of the coil between feed points in this example was 36 cm, providing a height to diameter ratio of less than one. In FIG. 2 the Teflon support rods 2 at 12:00, 3:00, 6:00 and 9:00 are not shown for clarity.

FIG. 2 shows how the width of the turns of the coil are expanded to for instance two inches along most of their length. This is done for instance by attaching copper tape 7 or the like, or by soldering copper strips to the windings. The resulting surface employs six convolutions or twists 8 in its path from the top to the bottom of the coil. The placement and frequency of the convolutions were also determined thru internal phantom measurements. In the FIG. 2 embodiment, the copper strips are aligned vertically in parallel between 4:30 and 7:30. The center turn is also vertical between 1:30 and 4:30 and from 7:30 to 10:30. The ends are oriented horizontally, that is, between 12:45 and 4:30 and from 7:30 to 11:15. The other parts are also arranged horizontally, that is between 10:30 and 4:30 and from 7:30 to 1:30.

The spacing between adjacent parts of loops in seen to be constant and wide for the first ¼ hour, and to then decrease to a constant and narrow spacing from 10:30 to 1:30 for a central part of the loop. For instance the spacing between the adjacent parts of the tape on the coil in the parallel central part can be one inch. To further concentrate heat in the center of the phantom, reflectors, desirably constructed of copper sheets or copper tape, were used.

Figure 3:
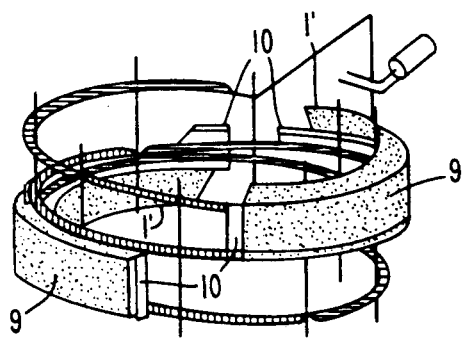
FIG. 3 shows two reflectors combined with the expanded turns of the coil of FIG. 2, according to the present invention.

In the embodiment of FIG. 3, two off-set reflectors 9 are shown. They extend up and down from the two center turns respectively, to complete a plane on the top and bottom of the coil with the half-turn that exists there. The reflectors 9 are supported on the top and bottom of the coil by attachment to a section of tubing 1' attached to the Teflon supporting rods and extending between 12:45 to 5:15 from 6:45 to 11:15. The reflectors 9 are separated from the turns of the coil by a plastic, e.g. polystyrene, strip 10, with dimension for instance of one inch thick by five inches wide, as indicated pattern in FIG. 3.

It was observed from heating results discussed further below that effective launch points for the RF wave occurred about ¾ turn from each end of the coil, that is, beginning at about 4:30 from the top and at about 10:30 from the bottom. This effect was enhanced by about a factor of 2 by use of the reflectors, resulting in uniform deep heating.

Figure 4:
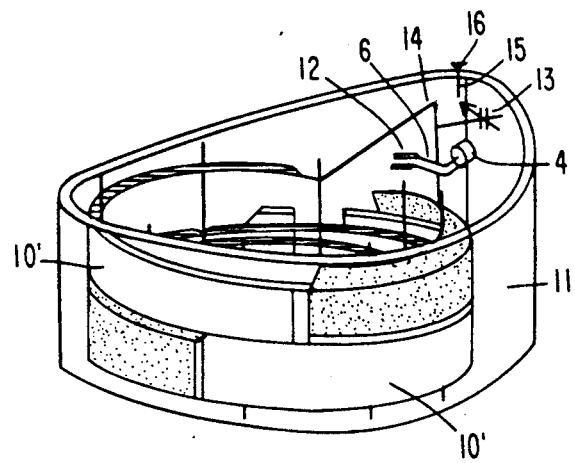
FIG. 4 shows an insulating shell surrounding the structure of FIG. 3, according to the present invention.

As shown in FIG. 4, the structure of FIG. 3 may be modified by first evening the front surface with two polystyrene strips 10', placed above and below the reflectors previously attached. This provides a flat vertical surface between 3:00 and 9:00. Secondly, the structure can be surrounded with an insulating shell, such as a one-inch-thick by 50 cm-high polystyrene shell 11, which is long enough to be joined by wire ties behind the input end. It is vertically centered over the coil, thereby extending 7 cm above and below the 36 cm separation at the feed points (the coil's maximum height). The coaxial connector 4 extends thru this juncture. Non-conducting tubing 12 is passed from the outside thru the polystyrene shell 11, and is slipped over the previously smoothed ends 6 of the copper tubing. A pipe clamp can be used to secure this joint if necessary. A lead wire from one end of a 200 pF variable capacitor 13 is soldered to the surface of the positive tubing leg 14 for instance approximately 10 cm above the coaxial input connector 4. The other end's lead wire is extended thru the polystyrene shell 11 for later attachment. This capacitor provides the only matching necessary for the standard 50 ohm RF generator and its coaxial cable. Depending on the physical construction of the variable capacitor, means must be provided for tuning it external to the eventually closed-in system. For example, a non-conducting rod 15 may be attached to the tuning mechanism of the variable capacitor 13, which extends upward to a height two inches above the top of the insulating shell where a knob 16 is attached. (If physically more convenient, the tuning rod can be brought out of the side through the polystyrene shell). The variable capacitor 13 can be either of the air or high-voltage vacuum type, the latter being more reliable.

Figure 5:
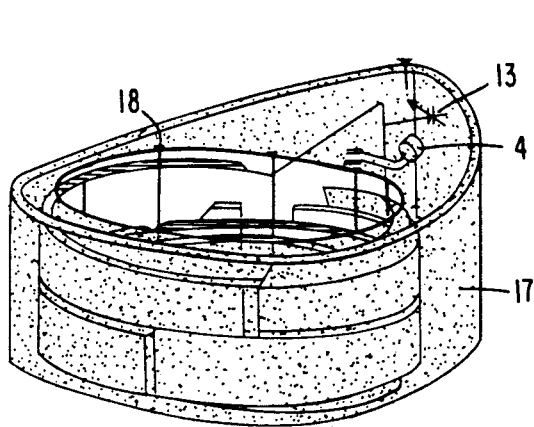
FIG. 5 shows a metallic screen surrounding the completed internal structure of FIG. 4, according to the present invention.

In the FIG. 5 embodiment, the polystyrene shell 11 (FIG. 4) and all but the upper and lower apertures are covered with a metallic, e.g. copper, screen material 17 (shown shaded). The copper screen is soldered to the outside of the coaxial input connector 4 at the juncture, thereby creating a ground plane and an RF shield. This results in virtually no emitted radio-frequency fields from the sides of the coil windings, an improvement in safety for the operators. The lead wire from the capacitor 13, previously passed thru the polystyrene shell, is also soldered to the copper screen at its juncture with it. If necessary, physical support of the capacitor thru screws passed from the copper screen into the capacitor's frame is completed at this time. The Teflon supports 2 are secured around both apertures to the copper screen 17 with wire ties 18. This construction adds physical strength, in addition to the operator safety it provides.

Figure 6:
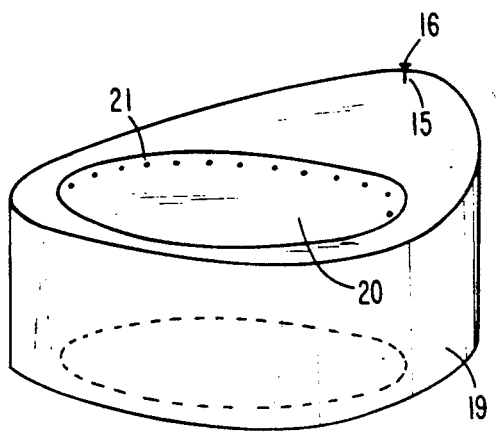
FIG. 6 shows a completed external structure of the sloped-helix coil, according to the present invention.

In FIG. 6 the preferred sloped-helix coil embodiment is shown. The copper screen 17 (FIG. 5) is covered with a rigid shell, such as a fiberglass shell 19. It is formed over the apertures defined by the copper screen 17 (FIG. 5) and extends into each of the apertures to a depth of approximately one inch. This provides a support on which to secure the inner liner of ⅛ inch thick Teflon sheet 20 using nylon screws 21. The outer shell provides additional structural support and protection for the system, and the inner shell protects the patient from coming into contact with the coil's windings during treatment. Also shown emerging from the fiberglass shell is the knob 16 attached through the non-conducting rod 15 to a tuning mechanism (not shown) of the variable capacitor.

A complete cycle of operation for testing is performed as follows, using a commercially available, standard fat-muscle simulated trunk phantom developed by the Center for Devices and Radiological Health for the National Cancer Institute.

The phantom is placed in the center of the aperture and is longitudinally centered along the length of the coil. The water lines are connected to an external supply and water circulated thru the coil. The coil is connected via a coaxial cable to a network analyzer or vector impedance voltmeter, or, alternatively, to a low-power RF generator and a power meter which is capable of reading reflected power. The frequency of the analyzer or generator was changed starting at about 70 MHz and extending to about 100 MHz. Coil-wire-length, double-wave resonance will occur at only one frequency, dependent on the coupling efficiency of the load or phantom and on the total wire length used in the coil. This condition was easily observed on the network analyzer display, wherein a definite impedance change is seen as the scanned frequency approaches the desired frequency. Similarly, if the power meter were alternatively used, it would show less reflected power as this frequency is reached. For a coil of these dimensions, and using this phantom, double-wave-length resonance occurs at a frequency of 81 MHz. Once the specific operating frequency is located, the variable capacitor, built into the coil's feed mechanism, is adjusted to obtain 50 ohms impedance. Alternatively, if the power meter were used, it would show very low to zero reflected power. The frequency may have to be slightly re-adjusted to achieve as good a match as possible. At this point, the high power RF generator is substituted for the network analyzer, or for the low power RF generator in the alternative embodiment, and the system is ready for use.

In a typical laboratory evaluation of this system, 100 watts of RF power are applied to the system for a period of one minute. This gives a sufficient temperature rise in the phantom to evaluate the heating pattern. Non-pertubing thermometers are inserted in the catheter tracks of the phantom.

Figure 7B:
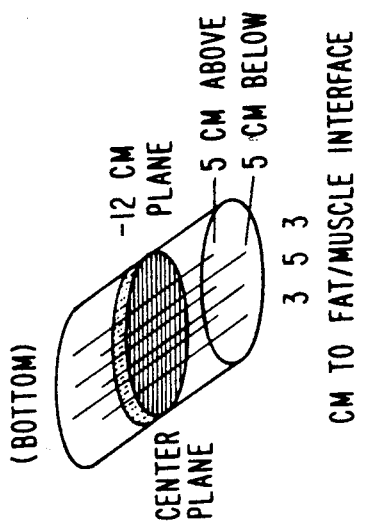
FIG. 7A and 7B show a phantom and location of its catheter tracks for internal temperature measurement used in evaluating the design of the sloped-helix, according to the present invention.
Figure 8B:
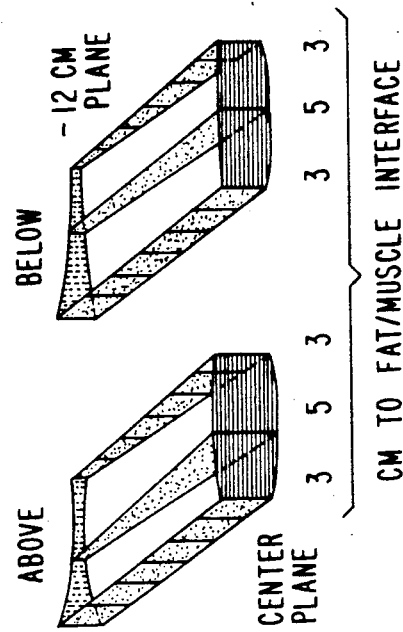
FIG. 8A and 8B show the results of heating a phantom by a diathermy device, according to the present invention.
Figure 7A:
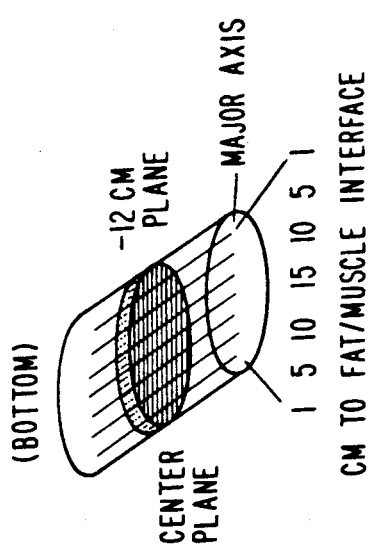
Figure 8A:
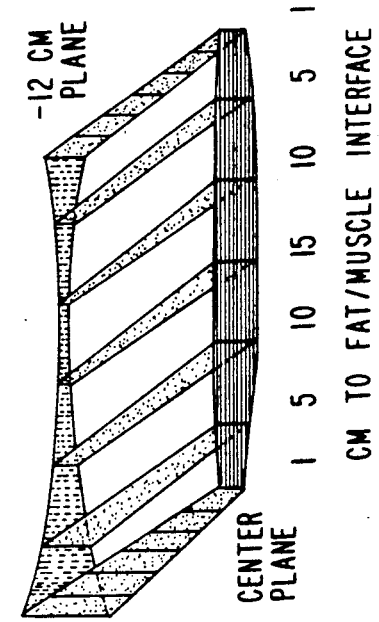

FIG. 7 shows a diagram of the phantom, with its dimensions shown on the graphs. The phantom has a 1 cm thick shell of simulated fat and is filled with simulated muscle material. The thermometer tips are initially placed so as to measure a selected plane, i.e., they are all inserted to the same depth. The temperature change in each of the 13 catheter tracks (7 tracks on the major axis and three tracks 5 cm above and below the major axis) is measured after one minute at 100 watts in the first selected plane, such as the −12 cm plane in FIG. 7. The probes are then withdrawn two centimeters and the measurements repeated in the next plane. This continues until a 12 cm track is mapped, that is, until the center plane in FIG. 7 is reached. As can be seen from the typical data which have been plotted in FIG. 8, the central plane heating is quite uniform, and no temperature change in the phantom was found to exceed the central heating by more than a factor of two. This held true for other 12 cm maps in the remainder of the phantom. This is an acceptable temperature variation for this size system.

Figure 9B:
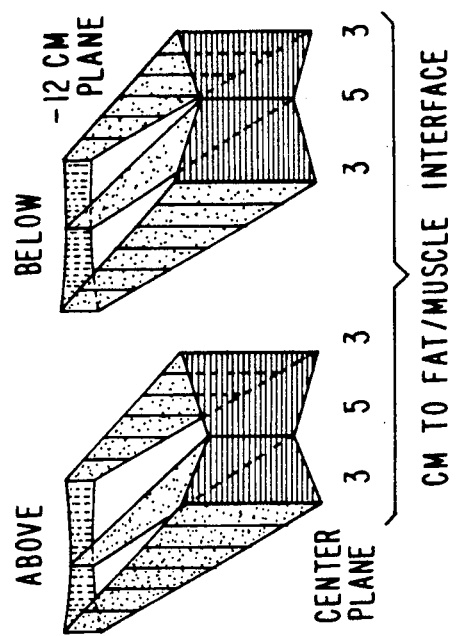
FIG. 9A and 9B show the results of heating a phantom by a prior art diathermy device.
Figure 9A:
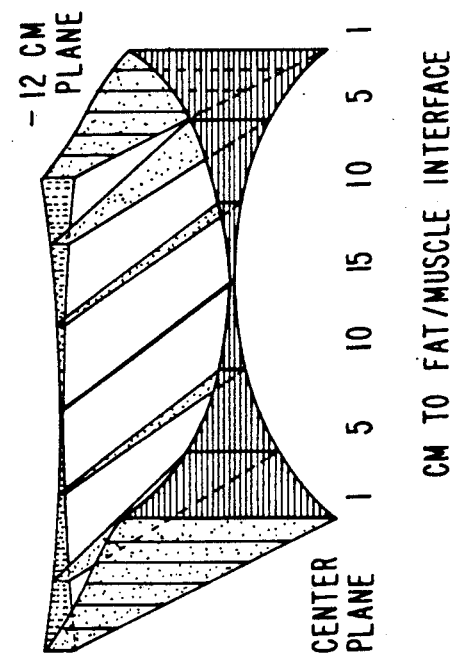

FIG. 9 shows the results using the prior art design of the patent above. The temperature distribution in the same trunk phantom under the same conditions is shown, but using a coil following the known design and with a one-to-one length to diameter ratio. The temperature change at certain points in the phantom was found to exceed the central temperature change by a factor of sixty.

The sloped-helix coil of the invention is used in therapy in substantially the same manner as in the testing mode as described above, except at higher RF power and for longer times. For instance, for treatment of deep-seated tumors in the trunk an RF treatment using the coil of the present invention would employ a power in the range of 600 to 2000 watts for 30 or more minutes.

The present invention constitutes an important advance in the use of coils for treating deep parts of the human body. The invention significantly employs the near-field radiation pattern of the coil, to achieve the launching of RF energy resulting in the deep uniform heating. The effect is understood to result from the length of the coil being equal to approximately two wavelengths of the RF waves, due to distributed charge patterns along the coil windings resulting in standing waves of electromagnetic energy. The coil configuration and the load determine the resonant frequency for these standing waves, at which point the entire load is resistive as seen by the RF generator. The purely resistive impedance of the entire load is then adjustable for instance by the variable capacitor as described above, to match loads to maximize power delivered to the part of the body being treated.

It will be obvious to those skilled in the art that various changes may be made without departing from the scope of the invention. The invention is not to be considered limited to what is shown in the drawings and described in the specification, but only by the scope of the appended claims.

I claim:

1. A coil for uniform and deep heating of a part of the human body with RF waves, comprising
   a sufficient size and shape as to be sloped-helix coil capable of surrounding a body part in its center of a conductor with n loops about a common axis, n being an odd integer equal to or greater than three, and feed lines extending in parallel from respective ends of respective end loops of said coil,
   wherein spacing between adjacent pairs of said loops in the direction of said axis decreases from a maximum at a respective distance from each of said ends of the respective end loops, and is constant for a central portion of said coil.

2. The coil of claim 1, of the double-wave type, wherein the length of said coil and feed lines is approximately equal to two wavelengths of said RF waves.

3. The coil of claim 2, n being three, and said central portion is approximately ¼ turn long and centrally located with respect to said ends of the coil.

4. The coil of claim 3, comprising a widening means capable of focusing a radio frequency, made of conducting material electrically connected to said loops and being twisted with respect to said loops to provide the same angular orientation thereof at least one common location along each of said loops.

5. The coil of claim 4, the twists of said widening means being such that
   respective first widened parts of said loops extend in said common location symmetrically through a plane containing said axis and said ends of said coils, with three such first parts oriented in parallel with said axis in a side of said coil across from said ends, and with two such first widened parts extending also parallel to said axis and symmetrically beyond said common location only for the central loop, and
   said widening means on the rest of said loops is oriented perpendicular to said axis.

6. The coil of claim 4, comprising two end parts of said widening means connected with said respective end parts of said coil, each of said end parts of said widening means being aligned.

7. The coil of claim 6, comprising the twists between said first parts and the rest of said widening means being provided at respective approximate angular positions of 1:30, 4:30, 7:30 and 10:30 about said axis on said central loop, and at 4:30 and 7:30 on each of the other loops, with respect to said ends of said loops being at 12:00.

8. The coil of claim 7, where end parts of said widening means of the other loops of said coil terminate approximately less than one hour before said 12:00.

9. The coil of claim 7, comprising a pair of reflectors each extending less than approximately ½ turn of a respective pair of adjacent loops, said pair of reflectors being approximately symmetrically oriented about a line perpendicular to and intersecting said axis of the coil and exiting said coil at a position midway between said ends of the coil.

10. The coil of claim 7, wherein are respective parts of said widening means are separated by approximately one inch along said central portion of said coil.

11. The coil of claim 2, each of said respective distances from each said end of the coil being equal to approximately ¼ turn.

12. The coil of claim 2, comprising a widening means capable of focusing a radio frequency, made of conducting material electrically connected to said loops.

13. The coil of claim 2, encased in an electrically insulating shell and a ground plane screen connected to one of said feed lines, said ground plane screen and said insulating shell having apertures thereon for allowing the respective part of the human body that is to be heated to be inserted into said coil.

14. The coil of claim 2, comprising a length to width ratio of less than approximately 1.

15. The coil of claim 2, comprising an oval cross section with a ratio of minor to major diameter of approximately 0.7.

16. The coil of claim 15, comprising effective launch points for said RF waves for said deep, uniform heating located in coil having parts having reflectors.

17. The coil of claim 1, each said respective distances from each said end of the coil being equal to approximately ¼ turn.

18. The coil of claim 1, comprising a pair of reflectors each extending less than approximately ½ turn of a respective pair of adjacent loops, said pair of reflectors being approximately symmetrically oriented about a line perpendicular to and intersecting said axis of the coil and exiting said coil at a position midway between said ends of the coil.

19. The coil of claim 1, comprising means for adjusting the wavelength of said RF waves to be approximately equal to one-half the length of said coil and said feed lines.

20. A method of using a device of claim 1, comprising selecting the wavelength of said RF waves to be approximately half the length of said coil and feed-lines; inserting a body part inside the sloped-helix coil in a manner such that the device is capable of heating said body parts; and providing radiofrequency power through said coil in an amount sufficient to provide deep heating to a body part.

* * * * *